United States Patent [19]

Ono et al.

[11] Patent Number: 5,011,923
[45] Date of Patent: Apr. 30, 1991

[54] POLYACETYL OLIGOSACCHARIDE DERIVATIVES

[75] Inventors: Mitsunori Ono, Kanagawa; Nobuo Suzuki, Saitama, both of Japan

[73] Assignee: Fuji Photo Film., Ltd., Kanagawa, Japan

[21] Appl. No.: 483,315

[22] Filed: Feb. 21, 1990

Related U.S. Application Data

[63] Continuation-in-part of Ser. No. 352,432, May 16, 1989, abandoned.

[30] Foreign Application Priority Data

May 17, 1988 [JP] Japan .................................. 63-120198
May 20, 1988 [JP] Japan .................................. 63-123045
Jun. 9, 1988 [JP] Japan .................................. 63-142587

[51] Int. Cl.$^5$ ...................... C07H 15/00; C07H 17/00
[52] U.S. Cl. .................................. 536/17.9; 536/17.2; 536/17.3; 536/17.4; 536/4.1; 536/17.7; 536/17.8
[58] Field of Search ............... 536/17.9, 4.1, 17.8, 536/17.2, 17.3, 17.4

[56] References Cited

U.S. PATENT DOCUMENTS 4,145,527 3/1979 Burns et al. .................... 536/122
4,147,860 4/1979 Farnham et al. ............... 536/119

FOREIGN PATENT DOCUMENTS 53-12831 2/1978 Japan .

Primary Examiner—Ronald W. Griffin
Assistant Examiner—Everett White
Attorney, Agent, or Firm—Sughrue, Mion, Zinn Macpeak & Seas

[57] ABSTRACT

A polyacetyl oligosaccharide derivative is described, represented by formula (I)

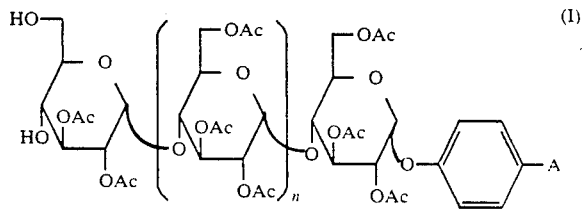

wherein A represents a nitro group or an amino group; Ac represents an acetyl group ($CH_3CO-$); and n represents 0 or an integer of from 1 to 8.

and a glucose heptamer having a biotin moiety at one end-group and a development nucleus-forming moiety at the other end-group which is derived from the compound of formula (I) is also described. The latter compound is useful as a substrate for enzyme activity assay systems.

3 Claims, 3 Drawing Sheets

POLYACETYL OLIGOSACCHARIDE DERIVATIVES

This is a continuation-in-part of application Ser. No. 07/352,432 filed May 16, 1989, now abandoned.

FIELD OF THE INVENTION

This invention relates to a polyacetyl oligosaccharide derivative having a hydroxyl group at the 4- and 6-positions of the non-reducing end-group and a p-nitrophenylglycosidic linkage or a p-aminonitrophenylglycosidic linkage at the reducing end-group, which is useful as a precursor of a substrate for assaying enzymatic activity. It further relates to an oligosaccharide derivative comprising a glucose heptamer having a biotin moiety and a development nucleus-forming moiety at each end-group thereof, which is derived from the above-described polyacetyl oligosaccharide derivative and is useful as a substrate for assaying enzymatic activity.

BACKGROUND OF THE INVENTION

Oligosaccharide derivatives in which the 4- and 6-hydroxyl groups in the non-reducing end-group thereof are unprotected, with the other hydroxyl groups being protected are described in *Liebigs Annalen der Chemie*, pp. 1910–1919 (1983). In the oligosaccharide derivatives disclosed, the reducing end-group has a phenylglycosidic linkage.

Oligosaccharide derivative in which the 4- and 6-hydroxyl groups at the non-reducing end-group are distinguished from other hydroxyl groups and the reducing end-group has a p-nitrophenylglycosidic linkage or a p-aminophenylglycosidic linkage are described in JP-A-60-54395, JP-A-60-87297, and JP-A-61-63299 (the term "JP-A" as used herein means an "unexamined published Japanese patent application"). These oligosaccharide derivatives are characterized in that only the 4- and 6-hydroxyl groups of the non-reducing end-group are protected.

No disclosure is found in any of the above-cited references with respect to polyacetyl oligosaccharide derivatives having hydroxyl groups at the 4- and 6-positions of their non-reducing end-group and a p-nitrophenylglycosidic linkage or a p-aminophenylglycosidic linkage at the reducing end-group.

Pentamers or heptamers of glucose having a detectable group, e.g., for a dye, at the reducing end-group are well known particularly in the field of clinical examination as described, e.g., in JP-A-53-12831, JP-A-60-54395, JP-A-60-78994, JP-A-60-237998, JP-A-61-83195, and JP-A 63-17895. However, syntheses of oligosaccharide derivatives having a functional group at each of the end groups that are different in function have not yet been reported.

SUMMARY OF THE INVENTION

A first object of this invention is to provide a polyacetyl oligosaccharide derivative having a hydroxyl group at the 4- and 6-positions of the non-reducing end-group thereof and a p-nitrophenylglycosidic linkage or a p-aminophenylglycosidic linkage at the reducing end-group thereof.

A second object of this invention is to provide a glucose heptamer having a biotin moiety exhibiting bioaffinity at the 4,6-position of the non-reducing end-group via a linking group and a group capable of forming development nuclei on photographic silver halide grains at the reducing end-group via a linking group.

These and other objects and effects of this invention will be apparent from the description hereinafter given.

The first object of this invention can be accomplished by a polyacetyl oligosaccharide derivative represented by formula (I):

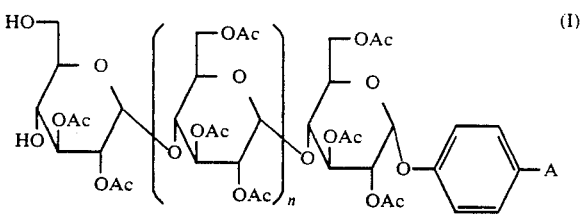

wherein A represents a nitro group or an amino group; Ac represents an acetyl group ($CH_3CO-$); and n represents an integer of from 0 to 7.

The second object of this invention can be accomplished by a glucose heptamer represented by formula (II).

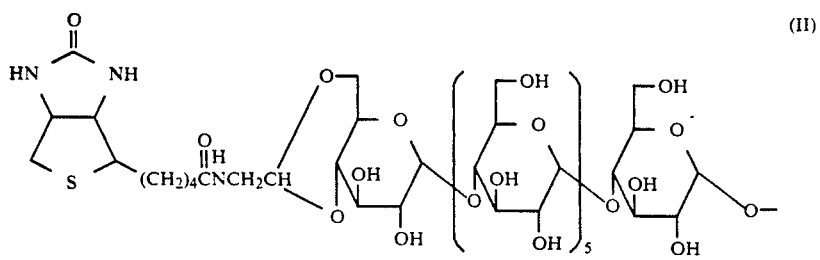

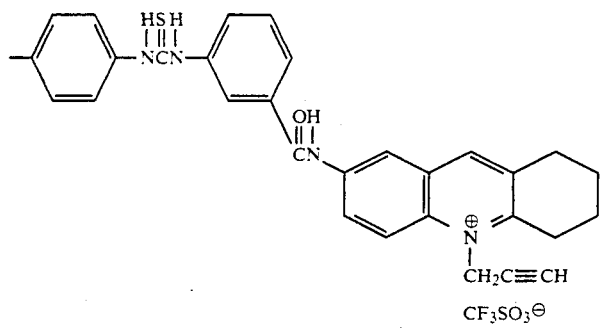

BRIEF DESCRIPTION OF THE DRAWINGS

In FIGS. 1 to 3 the abscissa indicates wavenumber (cm$^{-1}$) and the ordinate indicates absorbance.

DETAILED DESCRIPTION OF THE INVENTION

Figure 1:
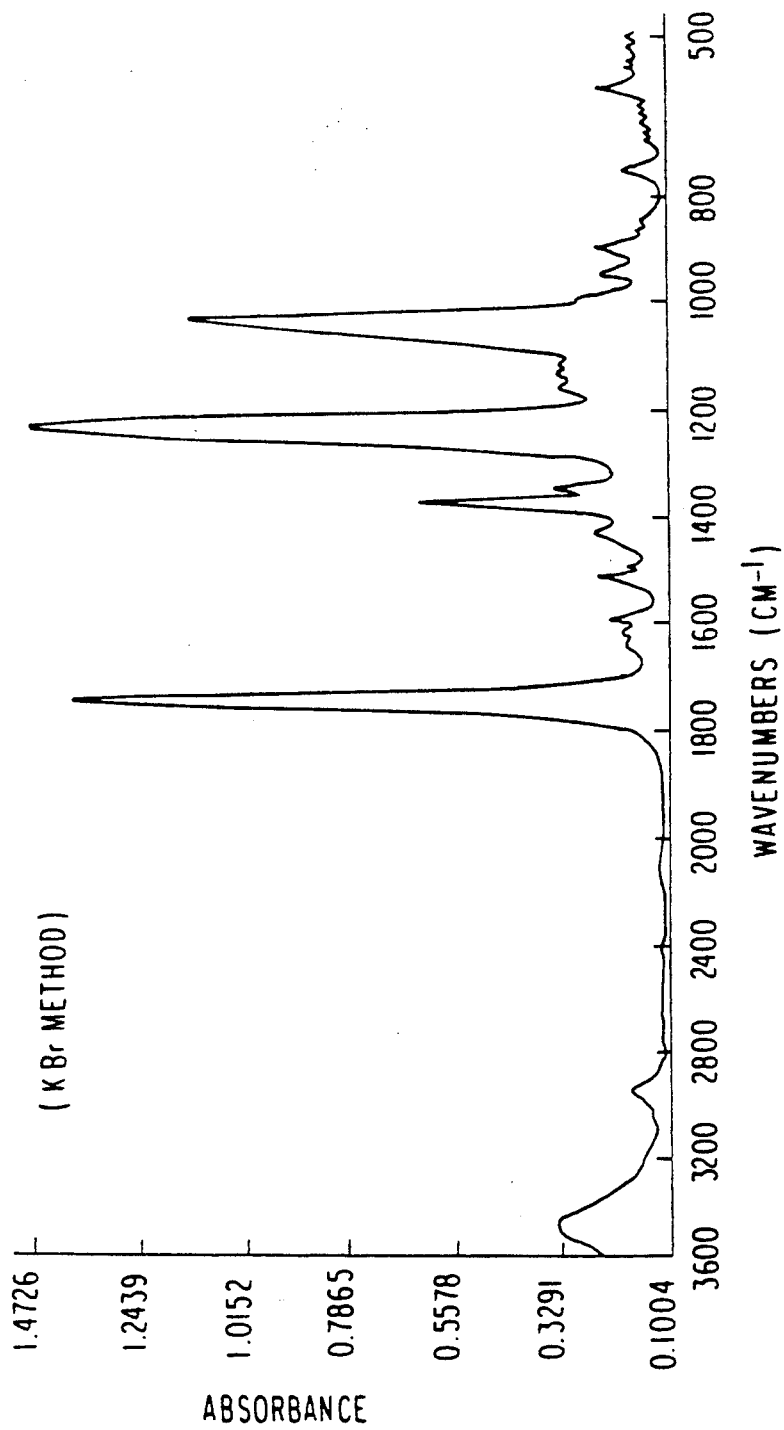
FIG. 1 is an infrared absorption (IR) spectrum (KBr method) of a compound used in the synthesis of the compounds of formula (I).

In formula (I), n preferably represents 1, 2, 4, or 5.

Synthesis of the compounds of formula (I) is shown below for illustrative purposes only, but not for limitation. In the following formulae, n and Ac are the same as defined above.

A compound represented by formula (X)

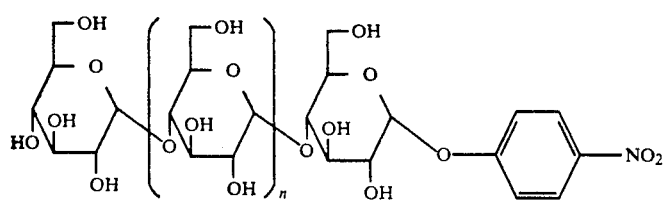

is reacted in the presence of α,α-dimethoxytoluene, p-toluenesulfonic acid, and dimethylformamide at 50° to 60° C. for 4 hours under reduced pressure. The compound represented by formula (X) where n is an integer of from 0 to 7 are commercially available and supplied by Seishin Pharmaceutical Co., Ltd. and Boehringer Mannheim GmbH. The product is then reacted in the presence of pyridine, acetic anhydride, and dimethylaminopyridine at room temperature for 20 hours. The reaction product is extracted with ethyl acetate and purified by column chromatography to obtain a compound represented by formula (Y).

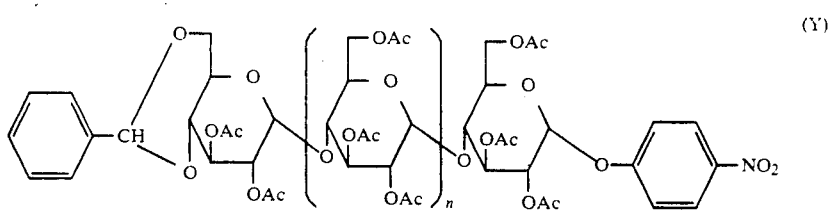

The resulting compound of formula (Y) is reacted in the presence of a 70% (by weight) aqueous solution of acetic acid at 90° C. for 1 hour. The reaction mixture is concentrated under reduced pressure, and the product is purified by column chromatography to obtain a compound of formula (I) wherein A is a nitro group.

The compound of formula (I) wherein A is an amino group can be obtained by reacting the compound of formula (I) wherein A is an nitro group in the presence of a 10% palladium-on-carbon (palladium catalyst supported on carbon in an amount of 10% based on the total amount of palladium and carbon), methanol, and hydrogen for 6 hours under normal pressure, collecting the crude reaction product by filtration, and recrystallizing the crude product from ethanol.

The compound represented by formula (II) can be synthesized from the compound of formula (I) wherein A is a nitro group and n is 5 in accordance with the reaction scheme shown below, but the method of synthesis is not limited thereto.

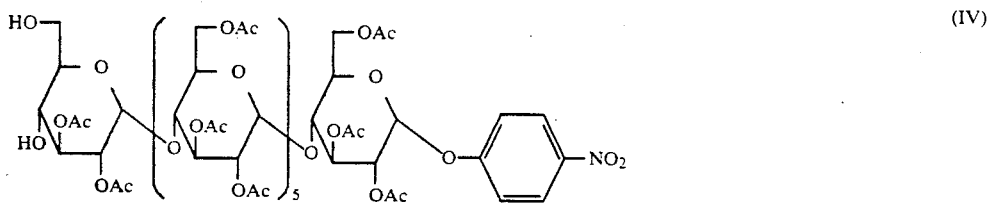
(IV)
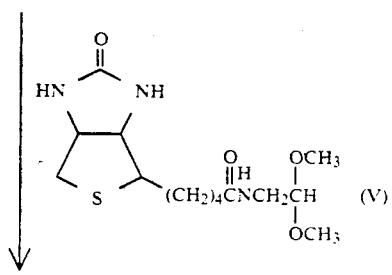
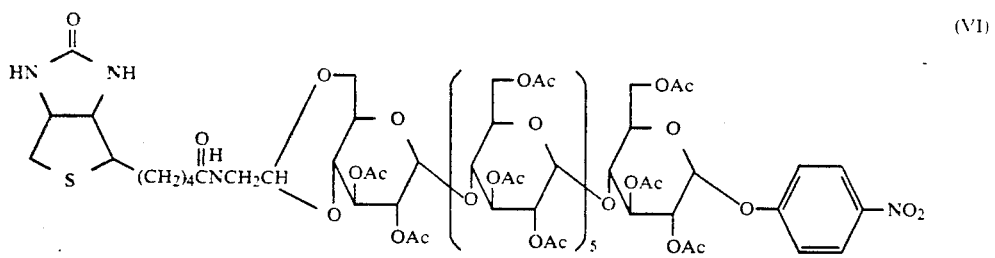
(VI)
Methanol
Sodium methoxide
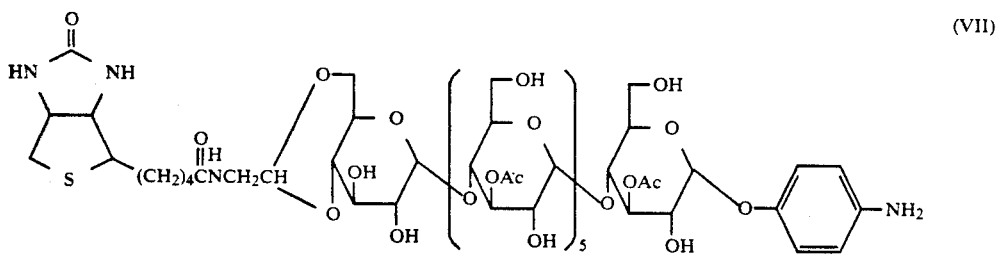
(VII)
Methanol
10% palladium-on-carbon
Hydrogen
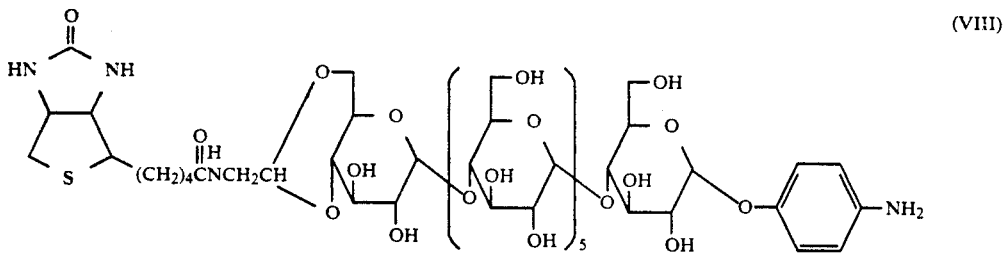
(VIII)

-continued

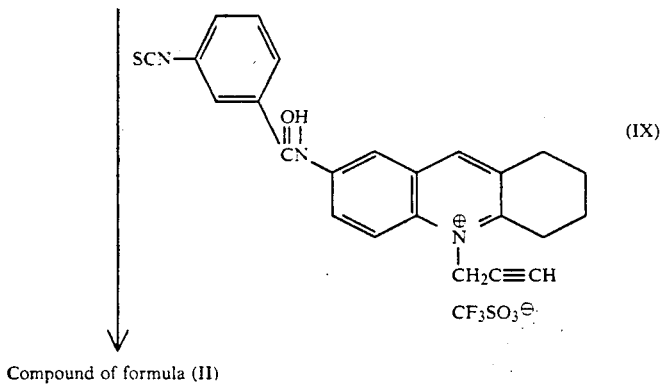

Compound of formula (II)

Since the compound of formula (I) has a nitro group or an amino group at the reducing end-group side, it is easy to link a functional compound thereto. The compound of formula (I) is therefore useful as a precursor capable of producing a highly sensitive substrate on linking to a highly sensitive functional compound.

A deacetylated compound derived from the compound of formula (I) is a substrate of which 1,4-glycosidic linkage is cleaved by the action of a specific enzyme.

In this case, when a functional compound, such as a compound showing bioaffinity, is linked to one or both of the 4- and 6-hydroxyl groups at the non-reducing end-group, then the cleaved non-reducing end-group and sugar section having the p-nitrophenylglycosidic linkage or p-aminophenylglycosidic linkage can be distinguished from each other by making use of the bioaffinity of the former section. That is, even if excess substrate exists in a solution, only the sugar section having the p-nitrophenylglycosidic linkage or p-aminonitrophenylglycosidic linkage can be isolated from products produced by enzymatic cleavage in an amount proportional to the quantity of an enzyme. The thus isolated sugar section having the p-nitrophenylglycosidic or p-aminophenylglycosidic linkage is then treated with an enzyme to release the p-nitrophenol or p-aminophenol. The enzymatic activity can thus be assayed by determining the amount of the released p-nitrophenol or p-aminophenol.

It is known to utilize determination of p-nitrophenol for assaying α-amylase activity as disclosed in JP-A-53-12831. Known methods for determining p-aminophenol include a ninhydrin method as described in *Journal of Biological Chemistry*, Vol. 67, p. 10 (1957).

Accordingly, the compounds of formula (I) are useful as intermediates for substrates to be used in enzyme activity assay systems utilizing 1,4-glycosidic linkage cleavage by specific enzymes.

Further, linking of a highly sensitive dye, fluorescent substance, or a photochemical nucleating agent to the amino group of the compound of formula (I) provides a substrate for determining a trace amount of p-aminophenol derivatives. The compounds of formula (I) are therefore also very useful as a precursor of substrates for highly sensitive enzyme assay systems.

The compounds of formula (II) are useful as substrates for assaying activities of specific enzymes capable of decomposing oligosaccharides.

Many conventionally employed enzyme activity assay systems comprise releasing a dye, a fluorescent substance, etc., from a sugar section cleaved by an enzyme, and colorimetrically determining the released substance. On the other hand, the enzyme assay system using the compounds of formula (II) as a substrate is a novel method comprising releasing a development nucleus-forming agent, which is well known in the field of silver halide photochemistry, on contact with an enzyme, leading the released development nucleus-forming agent to a silver halide photographic system where development processing is effected, and measuring the density of thus developed silver. This method utilizes the fact that the density of the developed silver and the concentration of the development nucleous-forming agent are proportional to each other. The biotin moiety of the compounds of formula (II) is used for removing an excess substrate remaining unchanged from the assay system. It is well known that biotin exhibits strong bioaffinity for avidin, a kind of glycoprotein. The unreacted substrate can easily be removed simply by contacting the reaction solution, after a given reaction time, with avidin or avidin fixed to a carrier. From this point of view, the compounds of formula (II) are of significance.

The present invention is now illustrated in greater detail reference to the following Examples, but it should be understood that the present invention is not deemed to be limited thereto.

EXAMPLE 1

Synthesis of Compound (I) (n=5; A=nitro group)

(A) Selective protection of 4,6-positions of non-reducing end-group:

In 200 ml of dimethylformamide (DMF) were dissolved 3.5 ml (1.5 eq.) of α,α-dimethoxytoluene, 544 mg (0.1 eq.) of p-toluenesulfonic acid, and 20 g of 4-nitrophenyl-α-D-maltoheptaoside having formula shown below (commercially available as $G_7$-PNP produced by Seishin Pharmaceutical Co., Ltd. or Boehringer Mannheim GmbH).

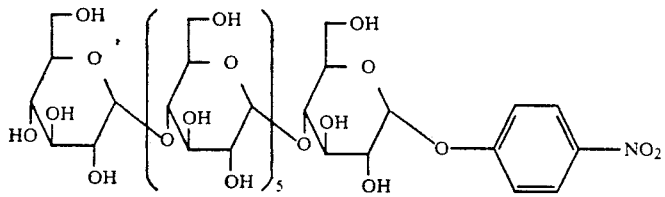

The mixture was stirred at 50° to 60° C. for 4 hours. After cooling to room temperature, 300 ml of pyridine, 120 ml of acetic anhydride, and 500 mg of dimethylaminopyridine were added to the reaction mixture, followed by allowing the reaction mixture to stand at room temperature for 20 hours. The reaction mixture was poured into 800 ml of ice-water and extracted twice with 500 ml portions of ethyl acetate. The organic layer was washed twice with 800 ml portions of a saturated sodium hydrogencarbonate (bicarbonate) produced aqueous solution, and then once with 800 ml of water, and dried over sodium sulfate. The sodium sulfate was removed by filtration, and the filtrate was concentrated under reduced pressure to obtain a pale yellow amorphous solid. The product was purified by silica gel column chromatography using hexane/ethyl acetate (1/2 by volume) as an eluent to obtain 20 g (yield: 58% based on 4-nitrophenyl-α-D-maltoheptaoside) of a compound shown below as a white powder. This compound was designated as Compound (a).

Compound (a)

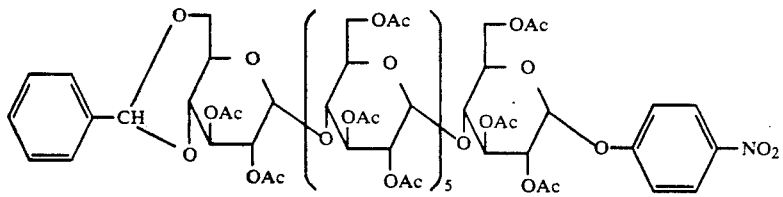

Melting Point: 141° to 145° C.
$[\alpha]_D^{31}$: +171° (CHCl$_3$, 0.98).
FAB-MS (first atom bombered mass spectrum): 2226 m/e [M+Na]+.
IR Spectrum: shown in FIG. 1.

(B) Selective removal of protecting group at 4,6-position of non-reducing end-group In 70 ml of a 70 wt % acetic acid aqueous solution was dissolved 6.7 g of Compound (a) as prepared in item (A) above, and the solution was stirred at 90° C. for 1 hour. The reaction mixture was concentrated under reduced pressure, and the resulting white solid was purified by silica gel column chromatography using hexane/ethyl acetate (1/20 by volume) as an eluent to obtain 5.2 g (yield: 80%) of a compound shown below as a white powder. This compound was designated as Compound (b).

Compound (b)

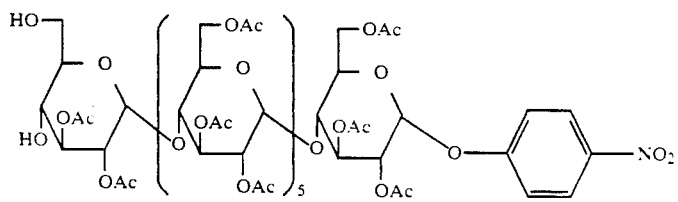

Melting Point: 144° to 149° C.
$[\alpha]_D^{22}$: +186° (CHCl$_3$, 1.02).
MS (FAB): 2136 m/e [(M+Na)+].
$^1$H-NMR (200 MHz; CDCl$_3$; standard: TMS) δ: 1.95–2.18

Figure 2:
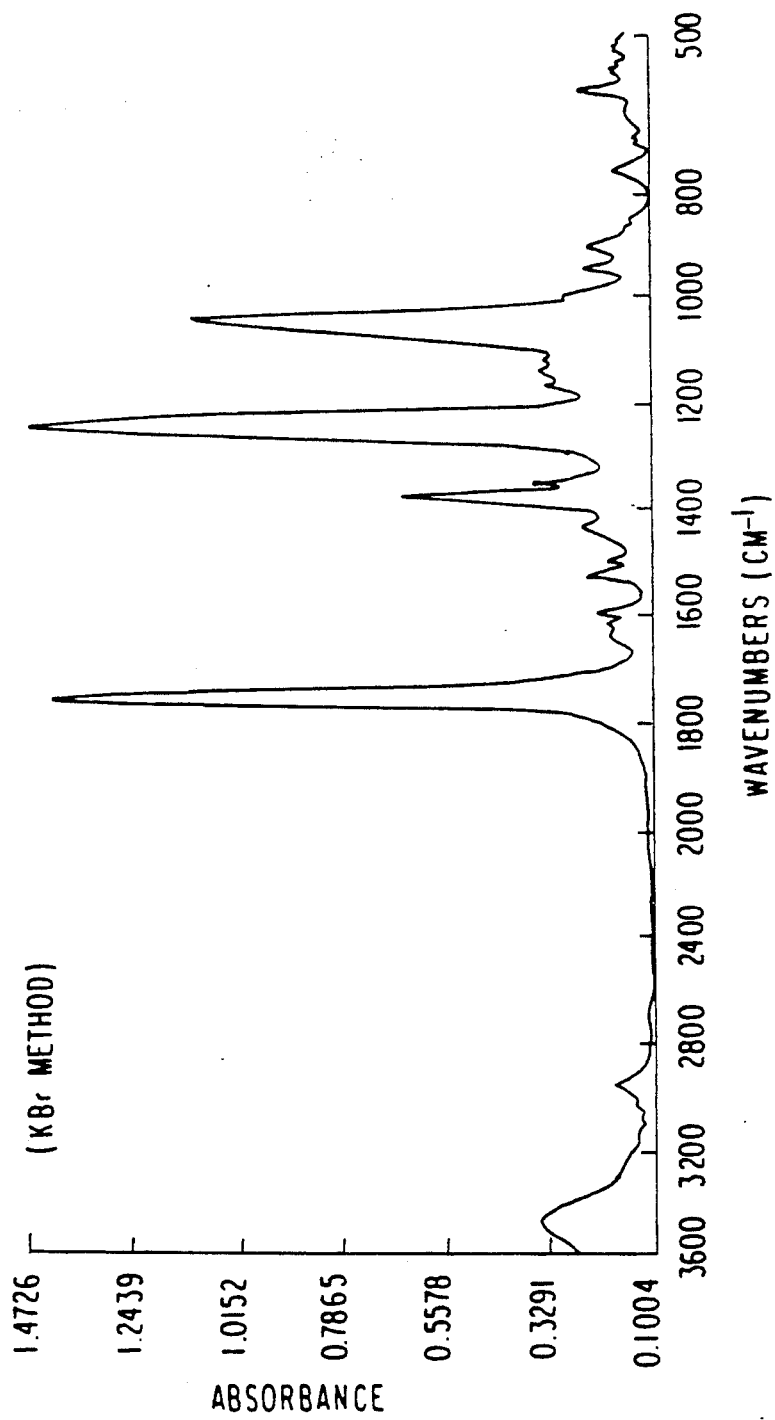
FIG. 2 is an FT-IR (Fourier transformation infrared) spectrum of the compound of formula (I) wherein n is 5 and A is a nitro group synthesized in Example 2.

(CCH$_3$, s, 60 H); 5.71 (H on anomer carbon, d, J=2 Hz, 1 H)
7.26, 8.23 (O—C$_6$H$_4$—(p-NO$_2$), AB-quartet. J=3 Hz, 4 H)
IR Spectrum (KBr method): shown in FIG. 2.

EXAMPLE 2

Synthesis of Compound (I) (n=5; A=amino group)

In 20 ml of methanol was dissolved 0.3 g of the compound (I) wherein n is 5 and A is a nitro group as obtained in Example 1, and 0.1 g of 10% palladium-on-carbon was added to the solution, followed by reacting in a hydrogen atmosphere under normal pressure for 6 hours at room temperature. The insoluble solid was separated from the reaction mixture by filtration through Celite and washed with methanol. The washing and the filtrate were combined and concentrated under reduced pressure. Recrystallization of the residue from ethanol gave 0.3 g (quantitative yield) of the desired compound of the formula shown below, in the form of white crystals.

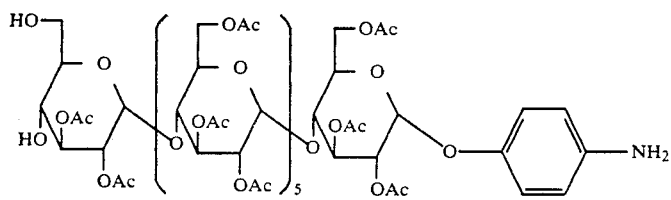

Melting Point: 140° to 144° C.
$[\alpha]_D^{22}$: 194° (CHCl₃, 1.0).
FAB-MS: 2106 (M+Na)⁺.
¹H-NMR (200 MHz; CDCl₃; standard: TMS): 2.02–2.24

s, 60 H); 7.19–7.29 (O—C₆H₄—(k-NH₂), m, 4 H).

EXAMPLE 3

A compound of formula (I), wherein n is 1, 2, or 4, and A is a nitro group was synthesized in the same manner as in Example 1, except for replacing the starting compound with p-nitrophenyl-α-D-maltotrioside, p-nitrophenyl-α-D-maltotetraoside, or p-nitrophenyl-α-D-maltohexaoside, respectively. Physical properties of the resulting compounds are shown in Table 1 below.

TABLE 1

| n | Physical Properties |
|---|---|
| 1 | Melting Point: 120–128° C.<br>$[\alpha]_D^{18}$: +123° (CHCl₃, 1.00) |
| 2 | Melting Point: 125–130° C.<br>$[\alpha]_D^{20}$: +154° (CHCl₃, 1.00) |
| 4 | Melting Point: 140–145° C.<br>$[\alpha]_D^{20}$: +165° (CHCl₃, 0.95) |

EXAMPLE 4

A compound of formula (I) wherein n is 0, 1 or 3 and A is an amino group was synthesized in the same manner as in Example 2, except for replacing the starting compound with each of the compounds shown in Table 2 below. Physical properties of the resulting compounds are also shown.

TABLE 2

| n | Starting Compound | Physical Properties |
|---|---|---|
| 1 | p-nitrophenyl-α-D-maltotrioside | Melting Point: 110–115° C.<br>$[\alpha]_D^{20}$: +110° (CHCl₃, 0.95) |
| 2 | p-nitrophenyl-α-D-maltotetraoside | Melting Point: 120–126° C.<br>$[\alpha]_D^{21}$: +140° (CHCl₃, 0.98) |
| 4 | p-nitrophenyl-α-D-maltohexaoside | Melting Point: 130–140° C.<br>$[\alpha]_D^{22}$: +145° (CHCl₃, 1.00) |

EXAMPLE 5

Synthesis of Compound (II)

In 30 ml of dry DMF, 5 g (2.5 mmol) of the compound of formula (I) wherein n is 5 and A is a nitro group were dissolved, i.e., the compound of formula (IV), as obtained in Example 1 and 4.1 g (12.5 mmol) of the compound of formula (V). Separately, 47 mg (0.25 mmol) of p-toluenesulfonic acid (PTS) monohydrate was heated to remove the water of crystallization as an azeotrope with chloroform-tetrahydrofuran, followed by drying in vauco to prepare PTS anhydride. The resulting PTS anhydride was dissolved in 5 ml of dry DMF, and the solution was added to the reaction solution of the compounds (IV) and (V) at room temperature while stirring. The mixture was heated at 50° to 60° C. for 5 hours under reduced pressure (20 to 30 mmHg) under stirring. After cooling, the reaction mixture was concentrated under reduced pressure and dried to obtain a pale brown solid. The solid was dissolved in a mixed solvent of chloroform and methanol (40/1 by volume), and any insoluble matter was removed by filtration. The filtrate was concentrated under reduced pressure, and the residue was purified by silica gel column chromatography using 400 g of Kiesel Gel 60 (trademark for product produced by Merck Co.) and chloroform/methanol (30/1 by volume) as an eluent. There were recovered 3.8 g of the compound (IV) remaining unreacted and 0.9 g (reaction yield: 70% recovery being taking into consideration) of the compound of formula (VI) as a white solid.

Melting Point: 145°–150° C.
$[\alpha]_D$: 151° (CHCl₃, 0.97).

In 250 ml of methanol was dissolved 850 mg (0.36 mmol) of the thus obtained compound (VI), and 2.1 ml of 0.1N sodium methoxide was added thereto while stirring. After allowing the mixture to stand at room temperature for 12 hours, the reaction mixture was neutralized with an ion exchange resin. The ion exchange resin was separated by filtration and thoroughly washed with methanol. The washing and the filtrate were combined and concentrated under reduced pressure to obtain 500 mg (quantitative yield) of the desired compound of formula (VII) in the form of pale yellow crystals.

In order to remove the yellow color originating in free p-nitrophenol, a small amount (about 10 ml) of methanol was added to the crystals, followed by throughly heating. Any insoluble crystals were collected by filtration and washed with cold methanol, to obtain 430 mg (78%) of the desired compound of formula (VII) as a whitish yellow crystal.

Melting Point: 139°–154° C.

In 2 ml of water was dissolved 300 mg (0.19 mmol) of the resulting compound (VII), and 20 ml of methanol was added thereto. To the solution was added 400 mg of 10% palladium-on-carbon as a reducing catalyst, and the mixture was stirred in a hydrogen atmosphere under normal pressure for 10 hours. The insoluble solid was separated by filtration using Celite and washed with a mixed solvent of methanol/water (10/1 by volume). The washing and the filtrate were combined and concentrated under reduced pressure. To the residue was added methanol, followed by heating. After removing any insoluble matter, the concentration under reduced pressure was further continued until crystals precipitated. To the resulting residue was added diethyl ether, followed by further crystallization. The thus formed crystals were collected by filtration to obtain the compound of formula (VIII) as a whitish yellow crystal.

Melting point: 181°–198° C.

In 6 ml of DMF was dissolved 150 mg (0.1 mmol) of the compound (VIII), and a solution of 65 mg (0.12 mmol) of the compound of formula (IX) in 0.5 ml of DMF was added dropwise to the solution. After stirring at room temperature for 1 hour, 150 ml of diethyl ether was added to the reaction mixture to precipitate crystals. Filtration of the mixture gave brown crystals, which were then washed successively with 200 ml of diethyl ether and 100 ml of acetonitrile to obtain the desired compound of formula (II) as a pale brown crystal.

Melting Point: 225°–256° C. (with decomposition).

FAB-MS: 1.933 m/e $(M+Na-CF_3SO_3)^+$.

$^1$H-NMR (200 MHz; $D_2O$; standard: TMS) δ: 1.30–2.35 (multiplet, methylene H of development nucleus forming moiety + methylene H of biotin = 16 H in total); 3.0–4.5 (multiplet, root H of OH + H at 4-position + methylene H of 6-position in sugar moiety = 42 H in total); 7.15–8.95 (multiplet, aromatic ring H = 12 H in total).

Figure 3:
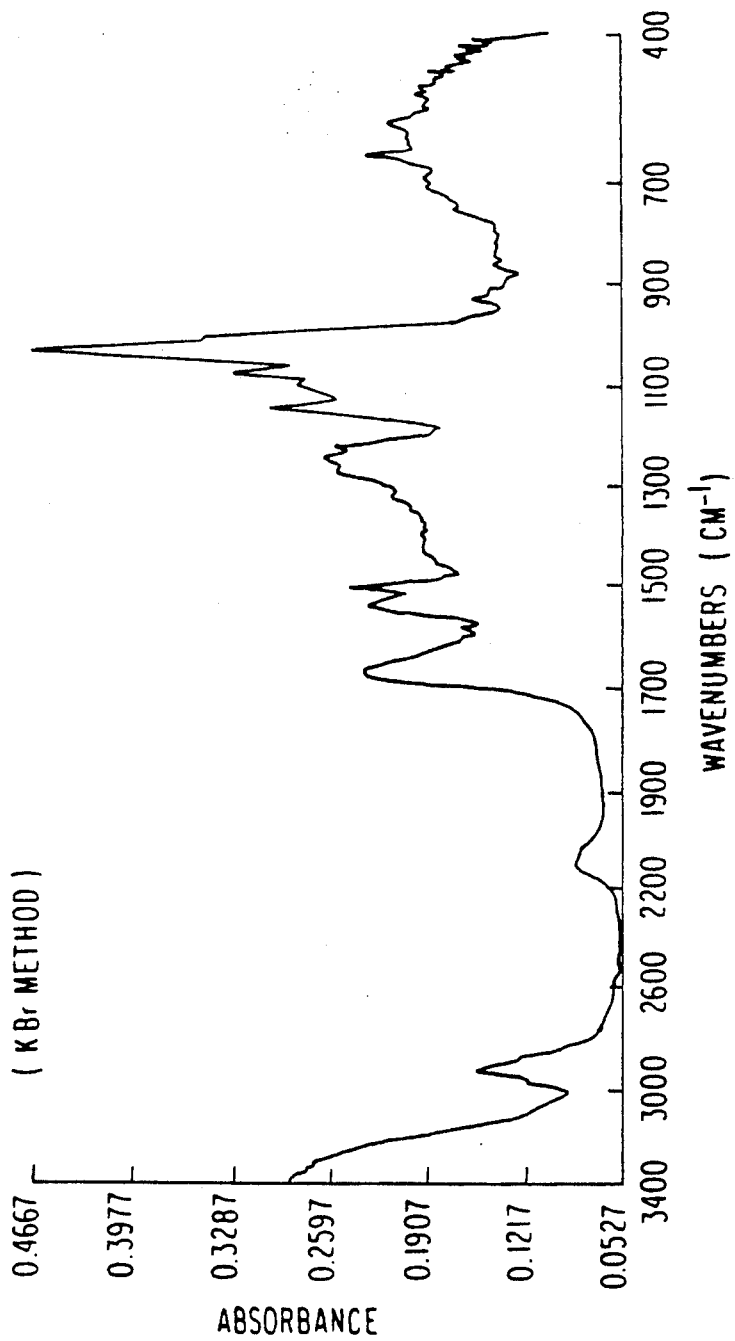
FIG. 3 is an FT IR spectrum of the compound of formula (II) synthesized in Example 5.

FT-IR Spectrum (KBr): shown in FIG. 3: 3400 cm$^{-1}$ (OH, NH), 2150 cm$^{-1}$ (terminal acetylene), 1670 cm$^{-1}$ (carbonyl of amidocarbonylurea).

As described above, the present invention provides polyacetyl oligosaccharide derivatives having a hydroxyl group at the 4- and 6-positions of the non-reducing end-group and a p-nitrophenyl glycosidic linkage or a p-aminonitrophenyl glycosidic linkage in the reducing end-group, which are useful as precursors for substrates for enzyme activity assay systems.

The present invention further provides oligosaccharide derivatives having a biotin moiety at one end-group and a development nucleus-forming moiety at the other end-group of a glucose heptamer, which are derived from the above-described polyacetyl oligosaccharide derivatives and are useful as substrates for enzyme activity assay systems.

While the invention has been described in detail and with reference to specific embodiments thereof, it will be apparent to one skilled in the art that various changes and modifications can be made therein without departing from the spirit and scope thereof.

What is claimed is:

1. A polyacetyl oligosaccharide derivative represented by formula (I)

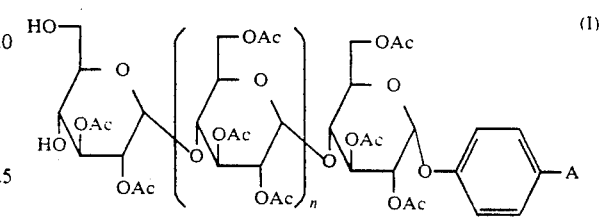

wherein A represents a nitro group or an amino group; Ac represents an acetyl group ($CH_3CO-$); and n represents an integer of from 0 to 7.

2. A polyacetyl oligosaccharide derivative as in claim 1, wherein n is 1, 2, 4 or 5.

3. A glucose heptamer represented by formula (II):

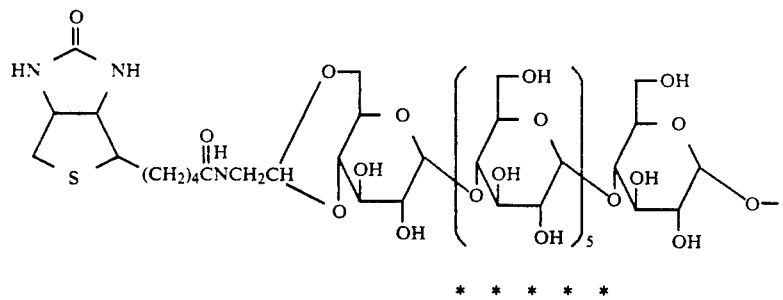

UNITED STATES PATENT AND TRADEMARK OFFICE
CERTIFICATE OF CORRECTION

PATENT NO. : 5,011,923
DATED : April 30, 1991
INVENTOR(S) : Mitsunori Ono, et al.

It is certified that error appears in the above-identified patent and that said Letters Patent is hereby corrected as shown below:

Column 14:

In claim 3, after line 3, complete formula (II) as follows:
--

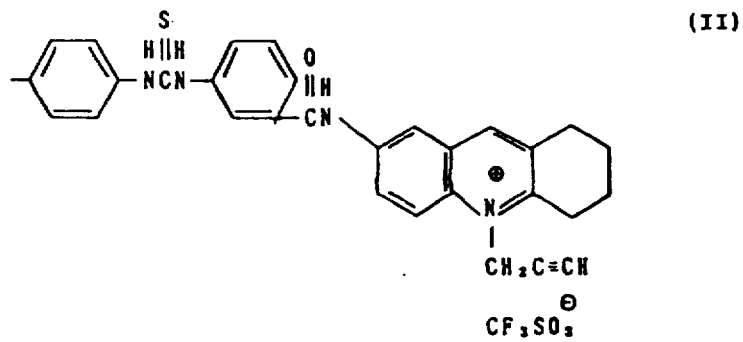

(II)

--.

Signed and Sealed this

Twenty-fourth Day of November, 1992

Attest:

DOUGLAS B. COMER

Attesting Officer

Acting Commissioner of Patents and Trademarks